(12) United States Patent
Venkatesh et al.

(10) Patent No.: US 8,747,895 B2
(45) Date of Patent: Jun. 10, 2014

(54) ORALLY DISINTEGRATING TABLETS OF ATOMOXETINE

(75) Inventors: Gopi M. Venkatesh, Vandalia, OH (US); Troy M. Harmon, Lansdale, PA (US); John Taylor, Dayton, OH (US)

(73) Assignee: Aptalis Pharmatech, Inc., Vandalia, OH (US)

( * ) Notice: Subject to any disclaimer, the term of this patent is extended or adjusted under 35 U.S.C. 154(b) by 1520 days.

(21) Appl. No.: 11/223,819

(22) Filed: Sep. 9, 2005

(65) Prior Publication Data
US 2006/0057199 A1    Mar. 16, 2006

Related U.S. Application Data

(60) Provisional application No. 60/609,312, filed on Sep. 13, 2004.

(51) Int. Cl.
*A61K 9/26* (2006.01)
*A61K 8/02* (2006.01)

(52) U.S. Cl.
CPC .................................. *A61K 8/0241* (2013.01)
USPC ........................................................ 424/469

(58) Field of Classification Search
USPC ........................................................ 424/469
See application file for complete search history.

(56) References Cited

U.S. PATENT DOCUMENTS

| | | |
|---|---|---|
| 3,184,386 A | 5/1965 | Stephenson |
| 3,558,768 A | 1/1971 | Klippel |
| 3,885,026 A | 5/1975 | Heinemann et al. |
| 4,078,051 A | 3/1978 | Pomot et al. |
| 4,138,475 A | 2/1979 | McAinsh et al. |
| 4,248,857 A | 2/1981 | DeNeale et al. |
| 4,292,017 A | 9/1981 | Doepel |
| 4,305,502 A | 12/1981 | Gregory et al. |
| 4,369,172 A | 1/1983 | Schor et al. |
| 4,371,516 A | 2/1983 | Gregory et al. |
| 4,389,330 A | 6/1983 | Tice et al. |
| 4,389,393 A | 6/1983 | Schor et al. |
| 4,542,042 A | 9/1985 | Samejima et al. |
| 4,556,678 A | 12/1985 | Hsiao |
| 4,587,118 A | 5/1986 | Hsiao |
| 4,628,098 A | 12/1986 | Nohara et al. |

(Continued)

FOREIGN PATENT DOCUMENTS

| | | |
|---|---|---|
| EP | 0052492 | 2/1984 |
| EP | 0166440 A2 | 1/1986 |

(Continued)

OTHER PUBLICATIONS

Bergain, Prim Care Companion J Clin Psychiatry 2004;6(2) 93-94.*
Kratochvil et al (Expert Opinion on Pharmacotherapy, vol. 4, No. 7 (2003) pp. 1165-1174).*
U.S. Appl. No. 11/213,266, filed Aug. 2005, Lai et al.
Chandra, "Examiner's first report on paten application 2005299490," 2 pages, Australia patent application No. 2005299490 (Mar. 12, 2010).

(Continued)

*Primary Examiner* — Benjamin Packard
(74) *Attorney, Agent, or Firm* — Cooley LLP

(57) ABSTRACT

A coated multi-particulate pharmaceutical dosage form such as an orally disintegrating tablet (ODT) presentation for delivering atomoxetine or a pharmaceutically acceptable salt thereof, a selective norepinephrine reuptake inhibitor indicated for the treatment of ADHD, into the body to maintain a therapeutically effective amount of atomoxetine in the plasm. The dosage form may comprise one or more populations of coated atomoxetine-containing particles (beads, pellets, granules etc.) providing a pre-designed rapid release profile after a predesigned lag-time of about 0 to 6 hours following oral administration.

29 Claims, 4 Drawing Sheets

(56) References Cited

U.S. PATENT DOCUMENTS

| | | |
|---|---|---|
| 4,661,647 A | 4/1987 | Serpelloni et al. |
| 4,670,459 A | 6/1987 | Sjoerdsma |
| 4,689,333 A | 8/1987 | Nohara et al. |
| 4,698,101 A | 10/1987 | Koivurinta |
| 4,708,867 A | 11/1987 | Hsiao |
| 4,713,248 A | 12/1987 | Kjornaes et al. |
| 4,716,041 A | 12/1987 | Kjornaes et al. |
| 4,728,512 A | 3/1988 | Mehta et al. |
| 4,743,248 A | 5/1988 | Bartoo et al. |
| 4,752,470 A | 6/1988 | Mehta |
| 4,757,090 A | 7/1988 | Salpekar et al. |
| 4,760,093 A | 7/1988 | Blank et al. |
| 4,780,318 A | 10/1988 | Appelgren et al. |
| 4,786,508 A | 11/1988 | Ghebre-Sellassie et al. |
| 4,800,087 A | 1/1989 | Mehta |
| 4,803,213 A | 2/1989 | Iida et al. |
| 4,824,675 A | 4/1989 | Wong et al. |
| 4,832,880 A | 5/1989 | Staniforth |
| 4,840,799 A | 6/1989 | Appelgren et al. |
| 4,851,226 A | 7/1989 | Julian et al. |
| 4,851,229 A | 7/1989 | Magruder et al. |
| 4,863,742 A | 9/1989 | Panoz et al. |
| 4,871,549 A | 10/1989 | Ueda et al. |
| 4,874,613 A | 10/1989 | Hsiao |
| 4,886,669 A | 12/1989 | Ventouras |
| 4,892,741 A | 1/1990 | Ohm et al. |
| 4,894,240 A | 1/1990 | Geoghegan et al. |
| 4,898,737 A | 2/1990 | Panoz et al. |
| 4,915,949 A | 4/1990 | Wong et al. |
| 4,938,968 A | 7/1990 | Mehta |
| 4,946,684 A | 8/1990 | Blank et al. |
| 4,957,745 A | 9/1990 | Jonsson et al. |
| 4,968,508 A | 11/1990 | Oren et al. |
| 4,971,805 A | 11/1990 | Kitanishi et al. |
| 4,983,401 A | 1/1991 | Eichel et al. |
| 5,006,345 A | 4/1991 | Lang |
| 5,011,692 A | 4/1991 | Fujioka et al. |
| 5,013,557 A | 5/1991 | Tai |
| 5,013,743 A | 5/1991 | Iwahi et al. |
| 5,017,122 A | 5/1991 | Staniforth |
| 5,017,381 A | 5/1991 | Maruyama et al. |
| 5,026,559 A | 6/1991 | Eichel et al. |
| 5,026,560 A | 6/1991 | Makino et al. |
| 5,039,540 A | 8/1991 | Ecanow |
| 5,045,321 A | 9/1991 | Makino et al. |
| 5,073,374 A | 12/1991 | McCarty |
| 5,075,114 A | 12/1991 | Roche |
| 5,079,018 A | 1/1992 | Ecanow |
| 5,082,669 A | 1/1992 | Shirai et al. |
| 5,084,278 A | 1/1992 | Mehta |
| 5,093,132 A | 3/1992 | Makino et al. |
| 5,104,648 A | 4/1992 | Denton et al. |
| 5,112,616 A | 5/1992 | McCarty |
| 5,133,974 A | 7/1992 | Paradissis et al. |
| 5,137,733 A | 8/1992 | Noda et al. |
| 5,149,542 A | 9/1992 | Valducci |
| 5,160,680 A | 11/1992 | Serpelloni et al. |
| 5,169,640 A | 12/1992 | France et al. |
| 5,178,878 A | 1/1993 | Wehling et al. |
| 5,204,121 A | 4/1993 | Bucheler et al. |
| 5,211,957 A | 5/1993 | Hagemann et al. |
| 5,213,808 A | 5/1993 | Bar-Shalom et al. |
| 5,229,131 A | 7/1993 | Amidon et al. |
| 5,229,135 A | 7/1993 | Philippon et al. |
| 5,238,686 A | 8/1993 | Eichel et al. |
| 5,252,337 A | 10/1993 | Powell |
| 5,256,699 A | 10/1993 | Murphy et al. |
| 5,260,068 A | 11/1993 | Chen |
| 5,260,069 A | 11/1993 | Chen |
| 5,275,827 A | 1/1994 | Spinelli et al. |
| 5,376,384 A | 12/1994 | Eichel et al. |
| 5,409,711 A | 4/1995 | Mapelli et al. |
| 5,433,959 A | 7/1995 | Makino et al. |
| 5,439,689 A | 8/1995 | Hendrickson et al. |
| 5,445,829 A | 8/1995 | Paradissis et al. |
| 5,464,632 A | 11/1995 | Cousin et al. |
| 5,466,464 A | 11/1995 | Masaki et al. |
| 5,470,584 A | 11/1995 | Hendrickson et al. |
| 5,472,708 A | 12/1995 | Chen |
| 5,478,573 A | 12/1995 | Eichel et al. |
| 5,489,436 A | 2/1996 | Hoy et al. |
| 5,501,861 A | 3/1996 | Makino et al. |
| 5,506,345 A | 4/1996 | Riley et al. |
| 5,508,040 A | 4/1996 | Chen |
| 5,529,790 A | 6/1996 | Eichel et al. |
| 5,536,507 A | 7/1996 | Abramowitz et al. |
| 5,567,441 A | 10/1996 | Chen |
| 5,576,014 A | 11/1996 | Mizumoto et al. |
| 5,609,883 A | 3/1997 | Valentine et al. |
| 5,612,059 A | 3/1997 | Cardinal et al. |
| 5,616,345 A | 4/1997 | Geoghegan et al. |
| 5,629,017 A | 5/1997 | Pozzi et al. |
| 5,639,475 A | 6/1997 | Bettman et al. |
| 5,643,630 A | 7/1997 | Hinzpeter et al. |
| 5,700,492 A | 12/1997 | Morimoto et al. |
| 5,720,974 A | 2/1998 | Makino et al. |
| 5,738,875 A | 4/1998 | Yarwood et al. |
| 5,747,068 A | 5/1998 | Mendizabal |
| 5,762,961 A | 6/1998 | Roser et al. |
| 5,788,987 A | 8/1998 | Busetti et al. |
| 5,807,577 A | 9/1998 | Ouali |
| 5,837,284 A | 11/1998 | Mehta et al. |
| 5,837,285 A | 11/1998 | Nakamichi et al. |
| 5,837,379 A | 11/1998 | Chen et al. |
| 5,840,329 A | 11/1998 | Bai |
| 5,876,759 A | 3/1999 | Gowan, Jr. |
| 5,891,474 A | 4/1999 | Busetti et al. |
| 5,900,252 A | 5/1999 | Calanchi et al. |
| 5,908,638 A | 6/1999 | Huber et al. |
| 5,968,554 A | 10/1999 | Beiman et al. |
| 6,024,981 A | 2/2000 | Khankari et al. |
| 6,024,982 A | 2/2000 | Oshlack et al. |
| 6,033,687 A | 3/2000 | Heinicke et al. |
| 6,039,979 A | 3/2000 | Gendrot et al. |
| 6,096,340 A | 8/2000 | Chen et al. |
| 6,099,859 A | 8/2000 | Cheng et al. |
| 6,099,863 A | 8/2000 | Gilis et al. |
| 6,099,865 A | 8/2000 | Augello et al. |
| 6,103,263 A | 8/2000 | Lee et al. |
| 6,106,861 A | 8/2000 | Chauveau et al. |
| 6,106,862 A | 8/2000 | Chen et al. |
| 6,123,962 A | 9/2000 | Makino et al. |
| 6,129,933 A | 10/2000 | Oshlack et al. |
| 6,136,345 A | 10/2000 | Grimmett et al. |
| 6,139,865 A | 10/2000 | Friend et al. |
| 6,139,877 A | 10/2000 | Debregeas et al. |
| 6,153,220 A | 11/2000 | Cumming et al. |
| 6,162,463 A | 12/2000 | Lippa |
| 6,169,105 B1 | 1/2001 | Wong et al. |
| 6,183,776 B1 | 2/2001 | Depui et al. |
| 6,190,692 B1 | 2/2001 | Busetti et al. |
| 6,221,392 B1 | 4/2001 | Khankari et al. |
| 6,221,402 B1 | 4/2001 | Itoh et al. |
| 6,228,398 B1 | 5/2001 | Devane et al. |
| 6,269,615 B1 | 8/2001 | Amborn et al. |
| 6,287,599 B1 | 9/2001 | Burnside et al. |
| 6,316,029 B1 | 11/2001 | Jain et al. |
| 6,328,994 B1 | 12/2001 | Shimizu et al. |
| 6,344,215 B1 | 2/2002 | Bettman et al. |
| 6,350,470 B1 | 2/2002 | Pather et al. |
| 6,350,471 B1 | 2/2002 | Seth |
| 6,365,182 B1 | 4/2002 | Khankari et al. |
| 6,368,625 B1 | 4/2002 | Siebert et al. |
| 6,368,628 B1 | 4/2002 | Seth |
| 6,372,253 B1 | 4/2002 | Daggy et al. |
| 6,391,335 B1 | 5/2002 | Pather et al. |
| 6,413,549 B2 | 7/2002 | Green et al. |
| 6,420,473 B1 | 7/2002 | Chittamuru et al. |
| 6,432,534 B1 | 8/2002 | Hayakawa et al. |
| 6,465,009 B1 | 10/2002 | Liu et al. |
| 6,465,010 B1 | 10/2002 | Lagoviyer et al. |
| 6,495,160 B2 | 12/2002 | Esposito et al. |
| 6,500,454 B1 | 12/2002 | Percel et al. |
| 6,500,457 B1 | 12/2002 | Midha et al. |

(56) References Cited

U.S. PATENT DOCUMENTS

| | | |
|---|---|---|
| 6,509,036 B2 | 1/2003 | Pather et al. |
| 6,531,152 B1 | 3/2003 | Lerner et al. |
| 6,551,617 B1 | 4/2003 | Corbo et al. |
| 6,579,535 B2 | 6/2003 | Valentine et al. |
| 6,596,311 B1 | 7/2003 | Dobetti |
| 6,602,521 B1 | 8/2003 | Ting et al. |
| 6,627,223 B2 | 9/2003 | Percel et al. |
| 6,641,838 B2 | 11/2003 | Pather et al. |
| 6,660,382 B2 | 12/2003 | Nouri et al. |
| 6,663,888 B2 | 12/2003 | Percel et al. |
| 6,663,893 B2 | 12/2003 | Corbo et al. |
| 6,740,341 B1 | 5/2004 | Holt et al. |
| 6,897,205 B2 | 5/2005 | Beckert et al. |
| 7,048,945 B2 | 5/2006 | Percel et al. |
| 8,071,128 B2 | 12/2011 | Ohta et al. |
| 2001/0007680 A1 | 7/2001 | Kolter et al. |
| 2001/0014340 A1 | 8/2001 | Ohta et al. |
| 2001/0046964 A1 | 11/2001 | Percel et al. |
| 2002/0054907 A1 | 5/2002 | Devane et al. |
| 2002/0077348 A1 | 6/2002 | Dean et al. |
| 2002/0142034 A1 | 10/2002 | Shimizu et al. |
| 2002/0187190 A1* | 12/2002 | Cade et al. ............... 424/480 |
| 2003/0064108 A1 | 4/2003 | Lukas et al. |
| 2003/0096791 A1 | 5/2003 | Gupte et al. |
| 2003/0113374 A1 | 6/2003 | Percel et al. |
| 2003/0134884 A1 | 7/2003 | Hazama et al. |
| 2003/0157173 A1 | 8/2003 | Percel et al. |
| 2003/0161888 A1 | 8/2003 | Fernandez et al. |
| 2003/0215500 A1 | 11/2003 | Ohta et al. |
| 2004/0047906 A1 | 3/2004 | Percel et al. |
| 2004/0121010 A1* | 6/2004 | Hirsh et al. ............... 424/468 |
| 2004/0122106 A1 | 6/2004 | Ohta et al. |
| 2004/0126427 A1 | 7/2004 | Venkatesh et al. |
| 2004/0131682 A1 | 7/2004 | Percel et al. |
| 2004/0137156 A1 | 7/2004 | Lee et al. |
| 2004/0242536 A1 | 12/2004 | Khoo et al. |
| 2005/0025824 A1 | 2/2005 | Percel et al. |
| 2005/0118268 A1 | 6/2005 | Percel et al. |
| 2005/0152974 A1 | 7/2005 | Boehm et al. |
| 2005/0232988 A1 | 10/2005 | Venkatesh et al. |
| 2005/0269722 A1 | 12/2005 | De Luigi Brushci et al. |
| 2006/0057199 A1 | 3/2006 | Venkatesh et al. |
| 2006/0078614 A1 | 4/2006 | Venkatesh |
| 2006/0105039 A1 | 5/2006 | Lai et al. |
| 2006/0121112 A1 | 6/2006 | Jenkins et al. |
| 2006/0233892 A1 | 10/2006 | Hendrix |
| 2006/0246134 A1 | 11/2006 | Venkatesh |
| 2006/0269607 A1 | 11/2006 | Percel et al. |
| 2007/0264358 A1 | 11/2007 | Wittlin |
| 2008/0069878 A1 | 3/2008 | Venkatesh et al. |
| 2009/0263480 A1 | 10/2009 | Lai et al. |
| 2011/0212171 A1 | 9/2011 | Venkatesh et al. |
| 2012/0128771 A1 | 5/2012 | Venkatesh |
| 2012/0135076 A1 | 5/2012 | Ohta et al. |

FOREIGN PATENT DOCUMENTS

| | | |
|---|---|---|
| EP | 0239361 A1 | 9/1987 |
| EP | 0349103 A1 | 1/1990 |
| EP | 0357369 A2 | 3/1990 |
| EP | 0391518 A2 | 10/1990 |
| EP | 0431877 A1 | 6/1991 |
| EP | 0453001 A1 | 10/1991 |
| EP | 0516345 A1 | 12/1992 |
| EP | 0538034 | 4/1993 |
| EP | 0553777 | 8/1993 |
| EP | 0721777 | 7/1996 |
| EP | 0650826 | 6/1997 |
| EP | 0815931 A1 | 1/1998 |
| EP | 0294493 A1 | 12/1998 |
| EP | 0914818 | 5/1999 |
| EP | 0914823 A1 | 5/1999 |
| EP | 1010423 A2 | 6/2000 |
| EP | 0582396 B1 | 1/2001 |
| EP | 1070497 A1 | 1/2001 |
| EP | 1072257 A1 | 1/2001 |
| EP | 1156786 | 11/2001 |
| EP | 1157690 A1 | 11/2001 |
| EP | 1366759 A1 | 12/2003 |
| EP | 0914823 b1 | 12/2004 |
| EP | 2319498 A1 | 5/2011 |
| FR | 2679451 | 1/1993 |
| FR | 2766089 | 1/1999 |
| FR | 2778848 A1 | 11/1999 |
| GB | 2053787 A | 2/1981 |
| GB | 8824392.8 | 9/1989 |
| GB | 2224207 A | 5/1990 |
| JP | 41-11273 B | 6/1966 |
| JP | 49-69819 | 7/1974 |
| JP | 55-129224 A | 10/1980 |
| JP | 56-014098 A | 10/1981 |
| JP | 61-143316 A | 7/1986 |
| JP | 62-61916 A | 3/1987 |
| JP | 62-50445 B2 | 10/1987 |
| JP | 62-242616 A | 10/1987 |
| JP | 62-246513 A | 10/1987 |
| JP | 62-252723 A | 11/1987 |
| JP | 63-162619 A | 7/1988 |
| JP | 63-270624 A | 11/1988 |
| JP | 1-503385 A | 11/1989 |
| JP | 1-313420 A | 12/1989 |
| JP | 2-500747 A | 3/1990 |
| JP | 2-164824 A | 6/1990 |
| JP | 2-172918 A | 7/1990 |
| JP | 2-289512 A | 11/1990 |
| JP | 3-240724 A | 10/1991 |
| JP | 4-224517 A | 8/1992 |
| JP | 5-271054 A | 10/1993 |
| JP | 5-310558 A | 11/1993 |
| JP | 653658 B2 | 7/1994 |
| JP | 6-321790 A | 11/1994 |
| JP | 7-69889 A | 3/1995 |
| JP | 07-124231 | 5/1995 |
| JP | 8-503482 A | 4/1996 |
| JP | 8-175978 A | 7/1996 |
| JP | 2002-154948 A | 5/2002 |
| JP | 2003-522141 A | 7/2003 |
| JP | 2005-508922 A | 4/2005 |
| NZ | 550608 A | 11/2005 |
| NZ | 554346 A | 5/2006 |
| WO | WO 88/08703 A1 | 11/1988 |
| WO | WO 88/08704 A2 | 11/1988 |
| WO | WO 92/10173 A1 | 6/1992 |
| WO | WO 93/00097 A1 | 1/1993 |
| WO | 93/12769 | 7/1993 |
| WO | WO 93/13758 A1 | 7/1993 |
| WO | WO 93/15724 A1 | 8/1993 |
| WO | 94/08576 | 4/1994 |
| WO | WO 94/12180 A1 | 6/1994 |
| WO | 97/41878 | 11/1997 |
| WO | WO 97/47287 A1 | 12/1997 |
| WO | 99/04763 | 2/1999 |
| WO | WO 00/25752 A1 | 5/2000 |
| WO | WO 00/33821 A1 | 6/2000 |
| WO | WO 00/42998 A1 | 7/2000 |
| WO | 00/51568 | 9/2000 |
| WO | 00/59486 | 10/2000 |
| WO | WO 01/13898 A2 | 3/2001 |
| WO | WO 01/72285 A1 | 10/2001 |
| WO | WO 01/80829 A2 | 11/2001 |
| WO | WO 02/13794 A1 | 2/2002 |
| WO | WO 02/43704 A1 | 6/2002 |
| WO | 02/057475 | 7/2002 |
| WO | 02/085336 | 10/2002 |
| WO | 03/013492 | 2/2003 |
| WO | WO 03/039520 A1 | 3/2003 |
| WO | 03/026613 | 4/2003 |
| WO | WO 03/041683 A2 | 5/2003 |
| WO | WO 03/043661 A1 | 5/2003 |
| WO | WO 03/047552 A2 | 6/2003 |
| WO | WO 2004/009058 A1 | 1/2004 |
| WO | WO 2004/022037 A1 | 3/2004 |

(56) References Cited

FOREIGN PATENT DOCUMENTS

| WO | WO 2004/087111 A1 | 10/2004 |
|---|---|---|
| WO | WO 2005/097064 A2 | 10/2005 |
| WO | WO 2005/105049 A2 | 11/2005 |

OTHER PUBLICATIONS

Villa, "Communication pursuant to Article 94(3) EPC," 4 pages, from European Patent Appl. No. 05818156.1, European Patent Office (Feb. 25, 2011).
Walsh, "Examination Report," 2 pages, from New Zealand Patent Appl. No. 589750, New Zealand Patent Office (Dec. 8, 2010).
Office Action, Mexico patent application No. MX/a/2007/004741, 3 pages, Mexico Patent Office (Oct. 12, 2010).
Welter, Office Action, 24 pages, U.S. Appl. No. 12/466,855, United States Patent and Trademark Office (Mar. 17, 2011).
Potenza, Examiner's first report on patent application No. 2005307052, 3 pages, Australia Patent Office (Mar. 15, 2010).
Schifferer, "Communication," 9 pages, from European Pat. Appl. No. 10184903.2, European Patent Office (Mar. 17, 2011).
Ahmed, Office Action, 5 pages, U.S. Appl. No. 10/453,848, United States Patent and Trademark Office (Sep. 5, 2008).
Ahmed, Office Action, 6 pages, U.S. Appl. No. 10/453,848, United States Patent and Trademark Office (Apr. 15, 2009).
Ahmed, Office Action, 8 pages, U.S. Appl. No. 10/453,848, United States Patent and Trademark Office (Mar. 31, 2010).
Berko, Office Action, 6 pages, U.S. Appl. No. 10/453,848, United States Patent and Trademark Office (May 23, 2005).
Fubara, Office Action, 4 pages, U.S. Appl. No. 10/334,052, United States Patent and Trademark Office (Dec. 1, 2003).
Oh, Office Action, 5 pages, U.S. Appl. No. 10/453,848, United States Patent and Trademark Office (Dec. 29, 2005).
Oh, Office Action, 6 pages, U.S. Appl. No. 10/453,848, United States Patent and Trademark Office (Dec. 12, 2007).
Oh, Office Action, 7 pages, U.S. Appl. No. 10/453,848, United States Patent and Trademark Office (Nov. 28, 2006).
Oh, Office Action, 7 pages, U.S. Appl. No. 10/453,848, United States Patent and Trademark Office (Jun. 13, 2007).
Villa, "European Search Report," 5 pages, from European Patent Appl. No. 11171982.9, European Patent Office, Munich, Germany (mailed Dec. 22, 2011).
Westerberg, Office Action, 11 pages, U.S. Appl. No. 11/500,892, United States Patent and Trademark Office (Mar. 26, 2010).
Westerberg, Office Action, 11 pages, U.S. Appl. No. 11/500,892, United States Patent and Trademark Office (Dec. 8, 2010).
Young, "International Search Report," 2 pages, PCT appl. No. PCT/US11/20493, United States Patent and Trademark Office (mailed Mar. 23, 2011).
Young, "Written Opinion of the International Searching Authority," 6 pages, PCT appl. No. PCT/US11/20493, United States Patent and Trademark Office (mailed Mar. 23, 2011).
Ahmed, Notice of Allowance, 8 pages, U.S. Appl. No. 13/282,271, United States Patent and Trademark Office (Sep. 24, 2012).
Bredefeld, Office Action, 28 pages, U.S. Appl. No. 11/256,653, United States Patent and Trademark Office (Aug. 28, 2012).
Albrecht, "International Search Report," 6 pages, from International Patent Appl. No. PCT/US02/31535, European Patent Office (Feb. 3, 2003).
Anwar et al., "Chronotherapeutic for Cardiovascular Disease," Drugs 55(5):631-643 (1998).
Fubara, "International Preliminary Examination Report," 3 pages, from International Patent Appl. No. PCT/US02/31535, European Patent Office (Jun. 19, 2003).
Ishino et al., "Design and Preparation of Pulsatile Release Tablet as a New Oral Drug Delivery System," Chem. Pharm. Bull. 40(11):3036-3041 (1992).
Nwokole et al., "Tolerance during 29 days of conventional dosing with cimetidine, mizatidine, famotidine or ranitidine," Aliment. Pharmacol. Ther. 4(Suppl. 1):29-45 (1990) Abstract only.

Ohira et al., "Effects of Various Histamine $H_2$-Receptor Antagonists on Gastrointestinal Motility and Gastric Emptying," J. Smooth Muscle Res. 29:131-142 (1993).
Rankin, "International Search Report," 6 pages, PCT International Application No. PCT/US02/39238, European Patent Office (May 8, 2003).
Ueki et al., "Nizatidine Comparably Enhances Postprandial Gastric Motility to Existing Gastroprokinetics in Dogs," Jpn. Pharmacol. Ther. 28(11):925-930 (2000).
Uhl, "International Search Report," 5 pages, International Patent Appl. No. PCT/US2006/016538, European Patent Office (Feb. 27, 2007).
Uhl, "Written Opinion of the International Searching Authority," 6 pages, International Patent Appl. No. PCT/US2006/016538, European Patent Office (Feb. 27, 2007).
Yamahara et al., "Effect of release rate on bioavailability of control-release multiple unit dosage forms," Yakuzaigaku 55(2):99-107 (1995).
Yamamoto et al., "The Effects of Nizatidine on the Function of Esophageal Motility in Patients with Gastroesophageal Reflux Disease (GERD)," Jpn. Pharmacol. Ther. 28(5):419-424 (2000).
Young, "International Preliminary Examination Report" 6 pages, PCT International Application No. PCT/US02/39238, United States Patent and Trademark Office (Apr. 27, 2005).
Young, "Written Opinion," 5 pages, PCT International Application No. PCT/US02/39238, United States Patent and Trademark Office (Jan. 13, 2005).
Zheng et al., "Influence of Eudragit® NE 30 D Blended with Eudragit® L 30 D-55 on the Release of Phenylpropanolamine Hydrochloride from Coated Pellets," Drug Development and Industrial Pharmacy 29(3):357-366 (2003).
Zimmer, "European Search Report," 3 pages, European patent appl. No. 01103129.1, European Patent Office (Jun. 9, 2001).
Zimmer, "International Search Report," 4 pages, PCT International Application No. PCT/US01/04012, European Patent Office (Jun. 19, 2001).
"Low Substituted Hydroxypropylcellulose," Official Monographs for Part II, 2001, NRF, JP, XIV, pp. 942-943.
Ahmed, "Interview Summary," 2 pages, from U.S. Appl. No. 10/356,641 (mailed Jul. 29, 2008).
Ahmed, "Interview Summary," 2 pages, from U.S. Appl. No. 10/356,641 (mailed May 15, 2009).
Ahmed, "Interview Summary," 3 pages, from U.S. Appl. No. 10/356,641 (mailed Sep. 8, 2006).
Ahmed, "Interview Summary," 4 pages, from U.S. Appl. No. 10/356,641 (mailed Aug. 2, 2006).
Ahmed, "Office Action Summary," 10 pages, from U.S. Appl. No. 10/356,641 (mailed Jan. 10, 2006).
Ahmed, "Office Action Summary," 13 pages, from U.S. Appl. No. 10/356,641 (mailed Apr. 14, 2008).
Ahmed, "Office Action Summary," 15 pages, from U.S. Appl. No. 10/356,641 (mailed Jun. 15, 2007).
Ahmed, "Office Action Summary," 20 pages, from U.S. Appl. No. 10/356,641 (mailed Aug. 19, 2009).
Ahmed, "Office Action Summary," 24 pages, from U.S. Appl. No. 10/356,641 (mailed Jun. 10, 2010).
Ahmed, "Office Action Summary," 44 pages, from U.S. Appl. No. 10/356,641 (mailed Dec. 11, 2008).
Ahmed, "Office Action Summary," 7 pages, from U.S. Appl. No. 10/356,641 (mailed Jun. 13, 2006).
Ahmed, "Office Action Summary," 7 pages, from U.S. Appl. No. 10/356,641 (mailed Nov. 30, 2006).
Bauer et al., Pharmarzeutische echnologie, $5^{th}$ Edition, 1997, Govi Verlag Frankfurt, pp. 164-166.
Bodmeier et al., "Theophylline Tablets Coated with Aqueous Latexes Containing Dispersed Pore Formers," J. Pharm. Sci. 79(10):925-928 (1990).
Citation in the Third Party Observation in the Opposition of European Patent No. EP 0914818 B1.
Database WPI, Section Ch, Week 198748, Derwent Publications, Ltd., London, GB; AN 1987-338131, XP002156870.

(56) References Cited

OTHER PUBLICATIONS

Duncan, "Examination Report," 2 pages, from New Zealand Patent Appl. No. 554346, New Zealand Patent Office, Wellington, New Zealand (mailed May 20, 2009).
Experimental data provided by Opponent I the Opposition of European Patent No. EP 0914818 B1.
Fell, Letter to The Editor, J. Pharm. Pharmacol. 1968, vol. 20, pp. 657-658.
FMC Corporation Product Specification for Avicel PH, 2005.
Foreign non-patent publication from Japanese textbook, 1989, Hirokawa Publishing Co.
Foreign non-patent publication Sysmex No. FP30SCJ001.
Gordon et al., "Effect of the mode of Super Disintegrant Incorporation on Dissolution in Wet Granulated Tables," J. Pharm. Sci. 82:220-226 (1993).
Gorman et al., An Evaluation of Croscarmellose as a Tablet Disintegrant in Direct Compression Systems, Drug. Dev. Ind. Pharm. 1982; vol. 8, pp. 397-410.
Handbook (Binran) of Granule, vol. 1, Ohmsha Ltd., p. 434 & 438 (May 3, 1975).
Kaneto et al., 2000, Latest Pharmacy, Hirokawa Publishing Co., 1 Edition, (Extract and English translation thereof).
Kawashima, "Low-Substituted Hydroxypropylcellulose as a Sustained-Drug Release Matrix Base or Disintegrant Depending on Its Particle Size and Loading in Formulation," Pharm. Res. 1993, vol. 10(3), pp. 351-355.
Korblum, "A New Tablet Disintegrating Agent," J. Pharm. Sci., Jan. 1973, vol. 62(1), pp. 43-49.
McKenna et al., "Effect of particle size on the compaction mechanism and tensile strength of tablets," J. Pharm. Pharmacol. Jun. 1982, vol. 34(6), pp. 347-351.
McKetta et al., "Table of Contents," Encyclopedia of Chemical Processing and Design (1989).
McKetta et al., Encyclopedia of Chemical Processing and Design, "Organic Phase Separation Conservation," p. 167 (1989).
Mitsuo et al., Pharmaceutics Manual, 1989, Pharmaceutics Manual, Nanzando Co. Ltd. (Extract and English translation thereof).
Observations issued by the European Patent Office on Aug. 16, 2002 regarding European Application No. 0914818 (Applicant Kyowa Hakko Kogyo Co., Ltd.).
Oh, "International Preliminary Report on Patentability," 5 pages, from International Appl. No. PCT/US2005/037084, United States Patent and Trademark Office, Alexandria, Virginia, USA (mailed Aug. 24, 2007).
Opposition Documents related to European Opposition of EP 091481B1 (Opposition file history as of Mar. 9, 2009, excluding duplicative, purely administrative documents (97 pages total), as indicated in the accompanying Information Disclosure Statement submitted herewith).
Pharmaceutical Excipients. London: Pharmaceutical Press, Electronic Version, 2006, Mannitol.
Pharmaceutical Excipients. London: Pharmaceutical Press, Electronic Version, 2006, Lactose Monohydrate.
Pharmaceutical Excipients. London: Pharmaceutical Press, Electronic Version, 2006, Croscarmellose sodium.
Rudnic et al., "Some Effects of Relatively Low Levels of Eight Tablet Disintegrants on a Direct Compression System," Drug. Dev. Ind. Pharm. 1981, vol. 7(3), pp. 347-358.
Rudnic et al., "Studies of the Utility of Cross Linked Polyvinlpolypyrrolidine as a Tablet Disintegrant," Drug Development and Industrial Pharmacy, 1980, vol. 6, No. 3, pp. 291-309.
Sato et al., "Anticonvulsant effects of tigabine, a new antiepileptic drug: the profile of action in the rat kindling model of epilepsy," Epilepsia 37(Supp. 3):110-111 (1996).
Schifferer, "Communication pursuant to Article 94(3) EPC," 3 pages, from European Patent Appl. No. 05851221.1, European Patent Office, Munich, Germany (mailed Oct. 13, 2009).
Schifferer, "International Search Report," 4 pages, from International Appl. No. PCT/US2005/037084, European Patent Office, Rijswijk, The Netherlands (mailed Jun. 1, 2006).
Schifferer, "Written Opinion of the International Search Authority," 6 pages, from International Appl. No. PCT/US2005/037084, European Patent Office, Munich, Germany (mailed Jun. 1, 2006).
Shangraw et al., "A new era of tablet disintegrants," Pharm. Technol. 1980, vol. 4(10), pp. 49-57.
Spear, "Office Action Summary," 16 pages, from U.S. Appl. No. 10/356,641 (mailed Dec. 8, 2004).
Tirkkonen and Paronen, "Enhancement of drug release from ethylcellulose microcapsules using solid sodium chloride in the wall," Int. J. Pharmaceutics 88:39-51 (1992).
Trottier and Wood, 2005, "Particle Size Measurement," Kirk-Othmer Encyclopedia of Chemical Technology (Extract of 1. Introduction; 2. Data Representation; 4. Measurement Methods; 8. Selection of Equipment).
van Kamp et al., "Improvement by super disintegrants of the properties of tablets containing lactose, prepared by wet granulation," Pharmaceutisch Weekblad Scientific Edition; 1983, vol. 5, pp. 165-171.
Villa, "Communication pursuant to Article 94(3) EPC," 3 pages, from European Patent Appl. No. 05818156.1, European Patent Office, Munich, Germany (mailed Jul. 1, 2009).
Villa, "International Search Report," 4 pages, from International Appl. No. PCT/US2005/038328, European Patent Office, Rijswijk, The Netherlands (mailed Sep. 15, 2006).
Villa, "Written Opinion of the International Search Authority," 5 pages, from International Appl. No. PCT/US2005/038328, European Patent Office, Munich, Germany (mailed Sep. 15, 2006).
Vrornans et al., "Studies on tableting properties of lactose," Pharmaceutisch Weekblad Scientific Edition; 1985, vol. 7, pp. 186-193.
Walsh, "Examination Report," 2 pages, from New Zealand Patent Appl. No. 554240, New Zealand Patent Office, Wellington, New Zealand (mailed Jun. 9, 2009).
Ware, "Office Action Summary," 12 pages, from U.S. Appl. No. 09/147,374 (mailed Oct. 14, 1999).
Ware, "Office Action Summary," 6 pages, from U.S. Appl. No. 09/147,374 (mailed Jun. 30, 2000).
Ware, "Office Action Summary," 6 pages, from U.S. Appl. No. 09/147,374 (mailed Aug. 29, 2001).
Ware, "Office Action Summary," 6 pages, from U.S. Appl. No. 09/147,374 (mailed Jun. 4, 2002).
Ware, "Office Action Summary," 8 pages, from U.S. Appl. No. 09/147,374 (mailed Apr. 18, 2001).
Welter, "Advisory Action Before the Filing of an Appeal Brief," 4 pages from U.S. Appl. No. 11/248,596 (mailed Oct. 13, 2010).
Welter, "Advisory Action Before the Filing of an Appeal Brief," 9 pages from U.S. Appl. No. 11/256,653 (mailed Sep. 27, 2010).
Welter, "Office Action Summary," 25 pages from U.S. Appl. No. 11/256,653 (mailed Mar. 18, 2010).
Welter, "Office Action Summary," 26 pages from U.S. Appl. No. 11/248,596 (mailed Mar. 19, 2010).
Welter, "Office Action Summary," 26 pages from U.S. Appl. No. 11/213,266 (mailed Nov. 13, 2009).
Welter, "Office Action Summary," 28 pages from U.S. Appl. No. 11/248,596 (mailed Jul. 10, 2008).
Welter, "Office Action Summary," 28 pages from U.S. Appl. No. 11/248,596 (mailed Apr. 29, 2009).
Welter, "Office Action Summary," 28 pages from U.S. Appl. No. 11/213,266 (mailed Apr. 6, 2009).
Welter, "Office Action Summary," 29 pages from U.S. Appl. No. 11/256,653 (mailed Jul. 10, 2008).
Welter, "Office Action Summary," 29 pages from U.S. Appl. No. 11/256,653 (mailed May 12, 2009).
Welter, "Office Action Summary," 29 pages from U.S. Appl. No. 11/213,266 (mailed Jul. 10, 2008).
Welter, "Office Action Summary," 33 pages from U.S. Appl. No. 11/213,266 (mailed Nov. 12, 2010).

* cited by examiner

ORALLY DISINTEGRATING TABLETS OF ATOMOXETINE

This application claims the benefit of U.S. Provisional Application No. 60/609,312, filed Sep. 13, 2004, the disclosure of which is hereby incorporated by reference.

TECHNICAL FIELD

This invention relates to a pharmaceutical composition preferably as an orally disintegrating tablet (ODT), comprising coated beads (taste-masked and/or pulsatile-release beads) of atomoxetine, or a pharmaceutically acceptable salt thereof, suitable for oral administration for the treatment of symptoms of attention deficit hyperactivity disorder (ADHD), which includes inattention, hyperactivity and impulsiveness.

BACKGROUND OF THE INVENTION

According to the American Psychiatric Association, about three to seven percent of children have ADHD. It is estimated that about four percent of adults have ADHD. Although the disorder is not well defined in adults, symptoms in adults include a lack of organization, daydreaming, irritability, and lack of motivation. Atomoxetine, the first new drug to be developed for ADHD in three decades, has a different mechanism of action from the stimulant-like drugs, such as methylphenidate, currently used to treat ADHD. Unlike stimulant-like drugs, atomoxetine does not appear to have a potential for abuse, and hence, is not classified as a controlled substance. Strattera®, Eli Lilly's product containing atomoxetine has been studied in children, adolescents and adults, and has been found safe and effective. Atomoxetine is rapidly absorbed after oral administration with an absolute bioavailability of 63% in EMs (extensive metabolizers) and 94% in PMs (poor metabolizers). Maximal plasma concentrations are reached approximately 1 to 2 hours after dosing with an estimated elimination half-life of about 5 hours. In these trials (including open-label and long-term studies), 5% EM patients and 7% of PM patients discontinued for adverse events. Typical adverse events included abdominal pain, constipation, dyspepsia, nausea, and vomiting. A standard high-fat meal typically decreases the rate of absorption without affecting the extent of absorption, resulting in a 10-37% lower $C_{max}$ and delayed $T_{max}$ by 3 hours.

Strattera is available in 10, 18, 25, 40, and 60 mg strengths as an immediate-release capsule dosage form. Administration of Strattera is initiated at a total daily dose of approximately 0.5 mg/kg and increased after a 3-day period to a target daily dose of approximately 1.2 mg/kg administered either as a single daily dose in the morning or as evenly divided doses in the morning and late afternoon/early evening. It is estimated that 50% of the population have problems of swallowing tablets or capsules (see Seager in Journal of Phramacol. and Pharm. 50, pages 375-382, 1998); especially it is hard to medicate children who have difficulty or are unwilling to swallow capsules. This leads to poor compliance, even non-compliance, with the treatment and thus has a negative impact on the efficacy of the treatment. ADHD patients are frequently advised to take Strattera with food to minimize the occurrence of adverse events such as nausea. Atomoxetine in Strattera has an extremely caustic and bitter taste. The bitter taste of atomoxetine precludes the medication from being easily sprinkled onto foods such as applesauce, a commonly used method of administering medications to children. Hence, administration of Strattera in pediatric patients is especially challenging for several reasons. Capsule dosage forms become sticky when wetted by saliva, and if the patient experiences difficulty swallowing the capsule on the first attempt, then the capsule must often be discarded. Furthermore, if a capsule partially dissolves in the child's mouth, as can result from unsuccessful swallowing or the capsule getting stuck in an orthodontic appliance, the resulting very unpleasant taste can make it difficult to persuade the child to take another dose. Since the product is expensive, this has both compliance and economic drawbacks. In addition, since the medicine is typically administered in the morning before the child begins his or her school day, incidences of nausea can be particularly debilitating. As such, there is a significant need for developing a modified-release dosage form, the administration of which would minimize the occurrence of adverse events and improve patient compliance, thus encouraging patient's adherence to the prescribed dosing regimen. An ideal dosage form would limit gastric upset and be easy to administer to children. Such a dosage form should have delayed or modified-release properties, to avoid significant dissolution in the stomach and/or to avoid high plasma peaks associated with administration of immediate release dosage forms, and have an easy-to-swallow, good tasting, orally disintegrating presentation to achieve higher patient compliance.

SUMMARY OF THE INVENTION

Atomoxetine is a selective norepinehrine reuptake inhibitor. It is the R(−) isomer and chemically (−)-N-Methyl-3-(o-tolyloxy)-propylamine hydrochloride. Strattera™, Eli Lilly's product containing atomoxetine, is indicated for the treatment of children, adolescents and adults with ADHD symptoms. Atomoxetine is rapidly absorbed after oral administration and has a half-life of about 5 hours. The administration of the current product, Strattera, as a single high dose in the morning can produce adverse events in patients and other issues associated with the administration of capsules containing extremely caustic, bitter-tasting atomoxetine, resulting in discontinuation of medication in some cases. The present invention provides a modified-release dosage form, preferably an ODT (orally disintegrating tablet) comprising coated atomoxetine having modified-release properties produced using one or more coacervation, granulation, extrusion-spheronization and fluid-bed coating processes. In conjunction with certain embodiments of the invention lower incidence of non-compliance and adverse events including abdominal pain, constipation, dyspepsia, nausea and vomiting which are generally associated with high $C_{max}$ and/or irritation to gastric mucosa in the patient upon administration of high doses of immediate release dosage forms required to achieve therapeutic efficacy may be achieved.

One embodiment is an ODT (orally disintegrating tablet) comprising coated atomoxetine particles (crystals, granules, drug-layered or extruded-spheronized beads) by coating atomoxetine with an enteric polymer, a water-insoluble polymer or a mixture thereof to take advantage of the predictable transit time of small, membrane-coated inert particles in the gastrointestinal tract, independent of gastric motility. However, a conventional chewable or modified-release matrix tablet formulation comprising coated multiparticulates (taste-masked, delayed-release or modified-release beads) containing atomoxetine suitable for once-daily dosing is also within the scope of this invention.

The multiparticulate pharmaceutical composition comprising coated microparticles (crystals, granules, pellets or beads) may be produced by applying a polymer membrane on atomoxetine particles (e.g., particles having a coating of atomoxetine and a binder) for imparting taste-masking and/or TPR properties. In one embodiment, these coated TPR particles alone or in combination with taste-masked IR particles will be blended with rapidly-dispersing microgranules and other pharmaceutically acceptable excipients and compressed into an ODT. The ODT thus produced will disintegrate on contact with the saliva in the oral cavity forming a smooth, easy-to-swallow dispersion containing coated microparticles. These coated microparticles will provide a single or bimodal (two pulses separated by 2 to 6 hours) plasma profile over several hours as they transit down the gastrointestinal tract. The granules or beads suitable for membrane-coating by coacervation or fluid-bed coating may be produced using a granulation, extrusion-spheronization, or drug-layering process.

One embodiment of the present invention provides a unit dosage form of modified-release atomoxetine as an ODT that would release the drug into an aqueous environment in one pulse or in two pulses separated by about 2-6 hours under in vitro conditions. In one embodiment, the TPR beads may be produced by a fluid-bed coating process following the procedures disclosed in U.S. Pat. No. 6,627,223, the contents of which are hereby incorporated by reference. Another embodiment of the present invention provides modified-release atomoxetine beads in the unit dosage form of an ODT (orally disintegrating tablet) which would rapidly disintegrate on contact with the saliva in the buccal cavity forming an easy-to-swallow suspension. The term "rapidly disintegrate" as used herein means that the ODT disintegrates in less than about 60 seconds. The directions for preparing rapidly-dispersing microgranules, blending these microgranules, modified-release (MR) atomoxetine beads (TPR beads alone or a mixture of taste-masked beads and TPR beads at a desired ratio) and other pharmaceutically acceptable excipients and compressing into tablets using a rotary tablet press are disclosed in co-pending U.S. patent application Ser. No. 10/827,106 filed Apr. 19, 2004, which is herein incorporated by reference. In a preferred embodiment, the microgranules additionally contain a disintegrant and still more preferably a so called super-disintegrant such as crospovidone, croscarmellose sodium, low substituted hydroxypropylcellulose and sodium starch glycolate in amounts of about 0.1 to 10% of the tablet. These and other embodiments, advantages and features of the present invention will become more clear when detailed description and examples are provided in subsequent sections.

DETAILED DESCRIPTION OF THE INVENTION

Figure 1:
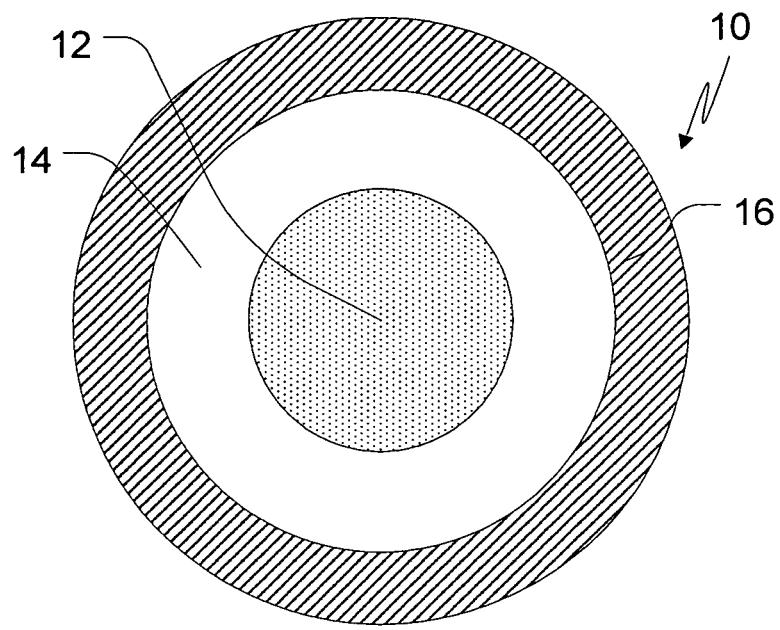
FIG. 1 illustrates a cross-section of a taste-masked bead in accordance with one aspect of the invention.

All documents cited are, in relevant part, incorporated herein by reference; the citation of any document is not to be construed as an admission that it is prior art with respect to the present invention.

As used herein, the term "atomoxetine" includes the base, pharmaceutically acceptable salts, polymorphs, stereoisomers and mixtures thereof.

As used herein, the term "immediate release" refers to release of greater than or equal to about 50%, preferably greater than about 75%, more preferably greater than about 90%, and in accordance with certain embodiments greater than about 95% of the active within about 2 hours, more particularly within about one hour following administration of the dosage form. The term can also refer to the release of active after a lag time of little or no release that occurs with a timed, pulsatile release dosage form characterized by an immediate release pulse after the designed lag time.

The term "immediate release (IR) bead" refers to an active-containing core particle. Components of the dosage forms described herein, such as TPR beads and taste-masked beads, may be prepared by coating IR beads to modify the release properties or other properties of the IR beads. Accordingly, dosage forms containing beads prepared from IR beads may or may not include any unmodified IR beads in the finished formulation.

In one embodiment, the active core of the dosage form of the present invention may be comprised of an inert particle coated with a drug-containing film-forming formulation. The amount of drug in the core will depend on the drug, the dose, and the capsule size. Those skilled in the art will be able to select an appropriate amount of drug for coating onto the core to achieve the desired dosage. In one embodiment, the inert particle may be a sugar sphere, a cellulose sphere, a silicon dioxide sphere or the like. Alternatively, the atomoxetine-containing core may be produced by granulation and/or by extrusion-spheronization of a composition containing atomoxetine or its salt, a binder and one or more hydrophilic fillers/diluents.

In one embodiment, the drug-containing particle may be coated with a combination of a water-insoluble polymer and an enteric polymer to produce TPR beads with a lag-time (release with a delayed-onset) of approximately 1 to 6 hours upon oral administration. The water-insoluble polymer and enteric polymer may be present at a weight ratio of from about 10/1 to about 1/1, preferably at a weight ratio of from about 2/1 to about 1/1. The membrane coating typically comprises from about 10% to about 60%, preferably from about 10% to about 30% by weight of the coated beads. Alternately, the drug core may simply be coated with an enteric polymer in the aforementioned amounts.

The unit dosage form according to the present invention may comprise TPR beads alone or in combination with taste-masked immediate release (IR) beads. Taste-masked IR beads will provide effective taste-masking in the buccal cavity and release atomoxetine in the gastrointestinal tract within approximately 2 hours, preferably within one hour following oral administration. The TPR beads will release atomoxetine over a period of up to approximately 1-4 hours in the gastrointestinal tract after a lag time of about 1-6 hours following oral administration.

One embodiment of the invention also provides a method of making an ODT (orally disintegrating tablet) dosage form comprising TPR beads alone or a mixture of taste-masked IR beads and TPR beads at a ratio of from about 30/70 to about 0/100, more particularly from about 20/80 to about 10/90 (IR beads/TPR beads). In accordance with one embodiment of the present invention, the method may include the steps of:

a. coating an inert particle (a sugar sphere, a cellulose sphere, a silicon dioxide sphere) with atomoxetine and a binder to form an active drug particle (IR bead);

b. coating IR bead with a solution of an enteric polymer such as HPMCP (hydroxypropyl methylcellulose phthalate) or a mixture of a water-insoluble polymer such as EC (ethylcellulose) and an enteric polymer at a ratio of about 10:1 to 1:1 to form a timed pulsatile-release drug particle (TPR bead);

c. when present, taste-masking IR beads by encapsulation with a water-insoluble polymer, such as ethylcellulose, by solvent coacervation or fluid-bed coating;

d. granulating a powder mixture of a sugar alcohol such as mannitol or a saccharide such as lactose and crospovidone, for example, using the disclosure in the co-pending U.S. patent application Ser. No. 10/827,106 filed Apr. 19, 2004 to produce rapidly-dispersing microgranules;

e. blending TPR beads from step (b) alone or in combination with taste-masked IR beads from step (c) at a ratio of from about 70/30 to about 100/0, more particularly from about 80/20 to about 90/10 to provide a desired plasma profile, rapidly-dispersing microgranules from step (d) and other pharmaceutically acceptable excipients; and f. compressing the blend from step (e) into orally disintegrating tablets comprising required dose of atomoxetine, which would rapidly disintegrate on contact with the saliva in the buccal cavity forming a smooth, easy-to-swallow suspension and exhibiting a plasma profile suitable for the treatment of ADHD with reduced incidence of adverse events including non-compliance by once-daily dosing in the morning.

When tested in accordance with the United States Pharmacopoeia dissolution procedure (USP Apparatus 1, Baskets@ 100 rpm, Drug Release Test 1 using 700 mL of pH 1.2 buffer for 2 hours followed by additional testing in 900 mL of pH 6.8), the ODT would exhibit the following:

a release of not more than about 25% of the total atomoxetine at 2 hours;

a release of not less than about 75%, preferably not less than about 85%, of the total atomoxetine after 8 hours.

In one embodiment, an aqueous or a pharmaceutically acceptable solvent medium may be used for preparing drug containing core particles. The type of film forming binder that is used to bind the water-soluble drug to the inert sugar sphere is not critical but usually water-soluble, alcohol-soluble or acetone/water soluble binders may be used. Examples of suitable binders include, but are not limited to, polyvinylpyrrolidone (PVP), polyethylene oxide, hydroxypropyl methylcellulose (HPMC), hydroxypropylcellulose (HPC) at concentrations of about 0.5 to 10 weight % based on the drug-layered bead. The drug substance may be present in this coating formulation in solution form or may be suspended at a solid content up to about 35 weight % depending on the viscosity of the coating formulation.

The active containing cores (beads, pellets or granules) thus obtained may be coated with one or more gastrosoluble, water-insoluble and enteric polymers to obtain coated (taste-masked) beads with a desired sustained-release, enteric-release or timed, pulsatile-release profile.

The taste-masking of atomoxetine particles may be achieved by coating IR beads with a taste-masking coating. In accordance with certain aspects of the invention, the taste-masking coating comprises a water-insoluble polymer such as ethylcellulose for a weight gain of about 5% to about 40%, preferably from about 10% to about 30% based on the coated particle. Examples of other water-insoluble polymers that can be used include, without limitation, cellulose acetate, cellulose acetate butyrate, polyvinyl acetate, and ammonio methacrylate copolymers sold under the trademarks Eudragit® RL and Eudragit® RS. No plasticizer is needed for forming membranes on the IR beads for effective taste-masking. One method for imparting effective taste-masking characteristics is coacervation by phase separation of ethylcellulose in cyclohexane. Examples of such a coacervation process are disclosed in U.S. Pat. No. 6,139,865, which is incorporated in its entirety by reference.

FIG. 1 illustrates a taste-masked bead 10 comprising an inert particle core 12 coated with a layer 14 containing the active in a binder. The inert particle core 12 and coating layer 14 make up the IR bead. The taste-masking coating 16 surrounds the IR bead and provides taste-masking without significantly changing the immediate release properties for the bead.

The TPR membrane coating, which would largely control the onset of drug release, typically comprises a water-insoluble polymer in combination with an enteric polymer. The water insoluble polymer may be selected from the group, which includes ethylcellulose, cellulose acetate, cellulose acetate butyrate, polyvinyl acetate, and ammonio methacrylate copolymers sold under the trademarks Eudragit® RL and Eudragit® RS. The enteric polymer may be selected from the group consisting of cellulose acetate phthalate, cellulose acetate succinate, polyvinyl acetate phthalate, hydroxypropyl methylcellulose (hypromellose) phthalate (HPMCP), hypromellose succinate (HPMCS), and methacrylic acid copolymers sold under the trademarks Eudragit® L and Eudragit® S. The ratio of water-insoluble polymer to enteric polymer for producing TPR beads may typically vary from about 10/1 to about 1/1, preferably from about 2/1 to 1/1, at a thickness of from about 10% to about 60%, preferably from about 10% to about 30% by weight of the coated bead.

Figure 2:
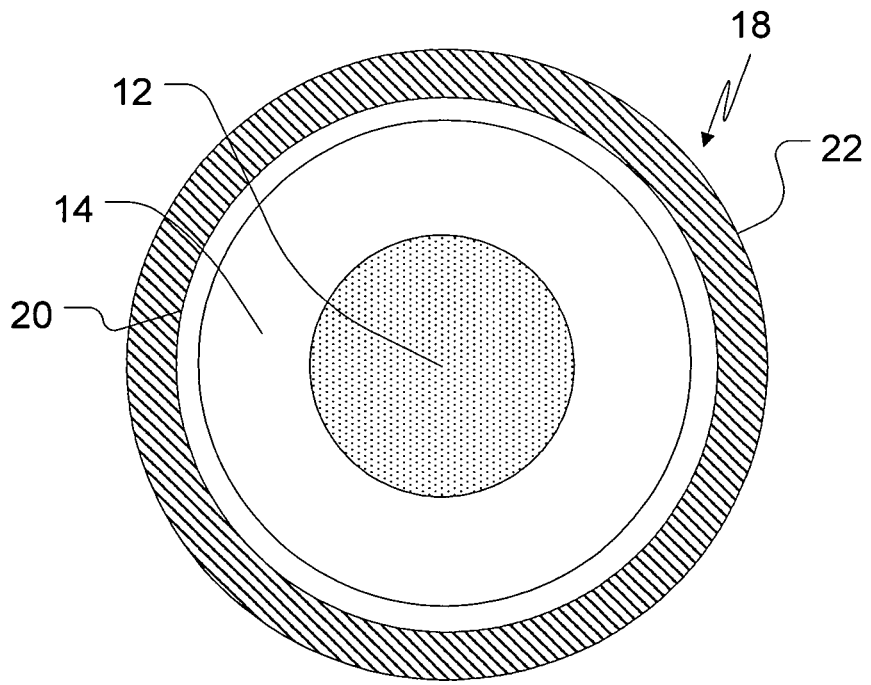
FIG. 2 illustrates a cross-section of a TPR bead in accordance with one aspect of the invention.
Figure 3:
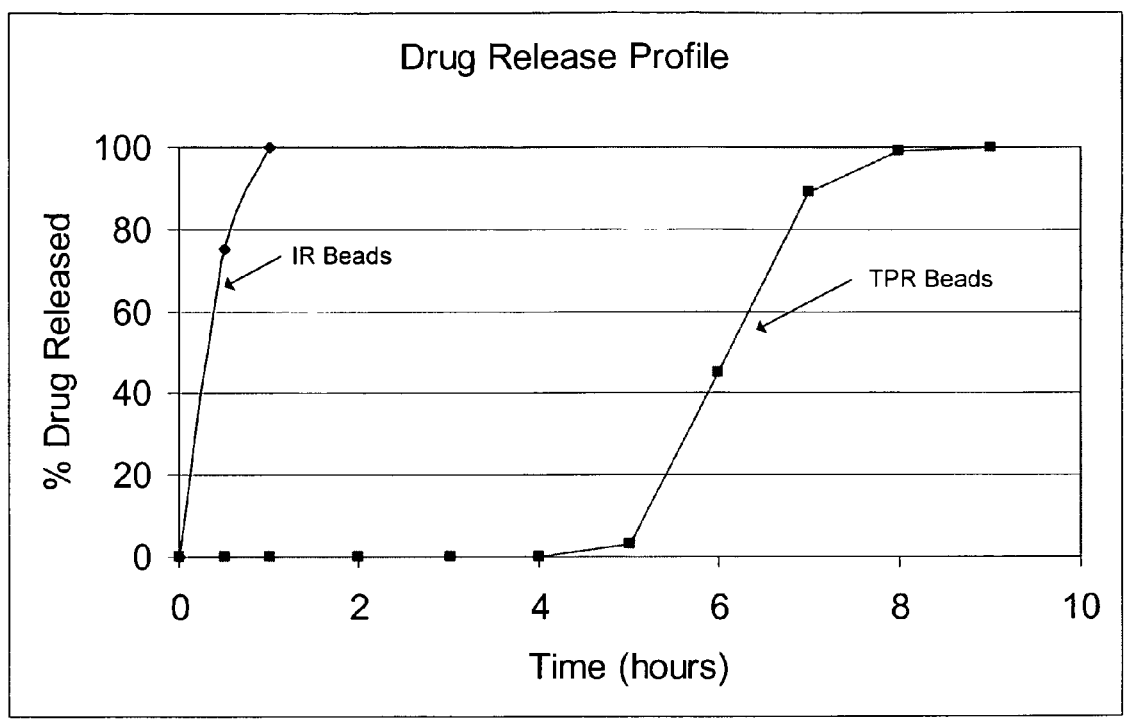
FIG. 3 is a theoretical drug-release profile for taste-masked beads and TPR beads in accordance with particular embodiments of the present invention.
Figure 4:
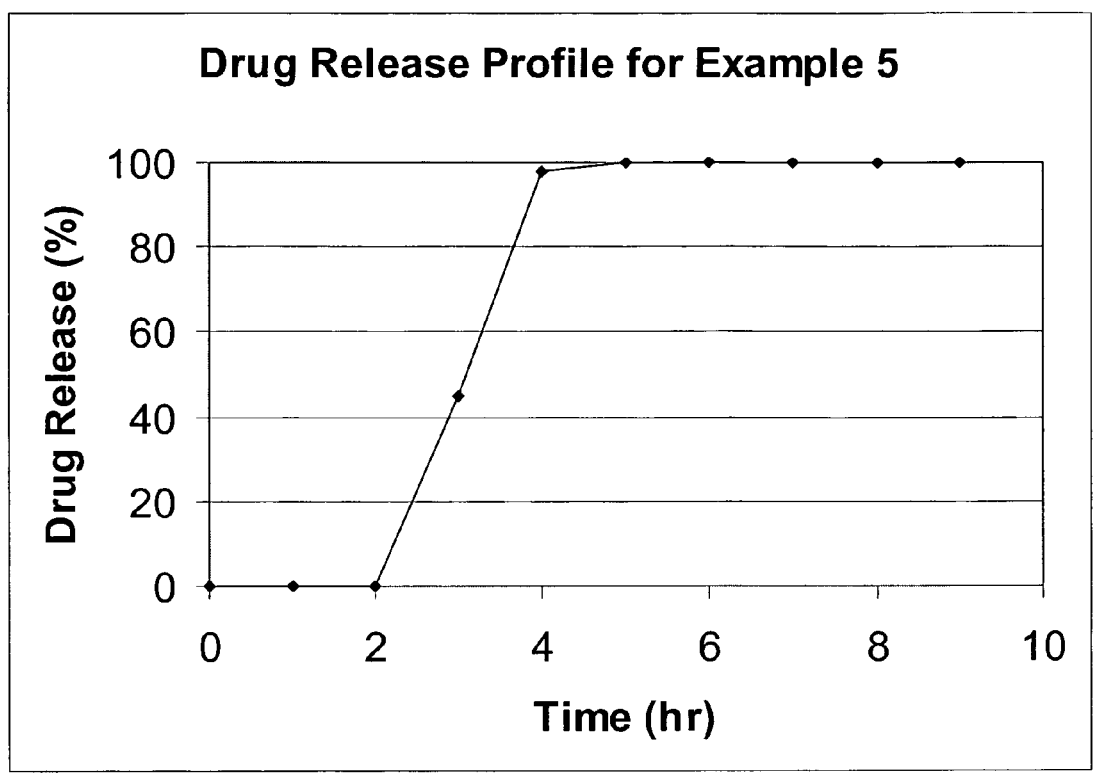
FIG. 4 shows a theoretical drug-release profile for MR Atomoxetine HCl ODT, 60 mg of Example 5.
Figure 5:
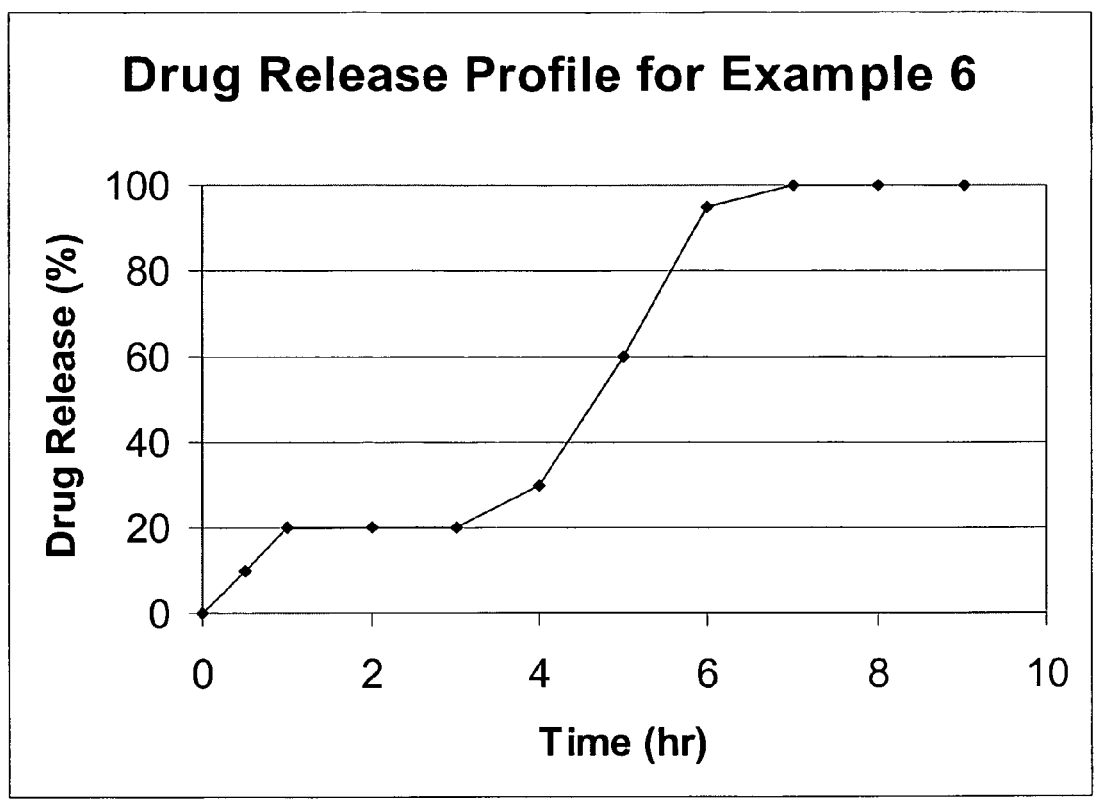
FIG. 5 illustrates a theoretical drug-release profile for 60 mg Atomoxetine HCl ODT containing 20% taste-masked beads and 80% TPR beads of Example 6.

A typical TPR bead 18 is illustrated in FIG. 2. The TPR bead 18 as shown includes an inert particle core 12, a layer of active agent and binder 14, a seal coat layer 20 and an external lag-time coating 22.

The membranes and coatings described herein may also include one or more plasticizers. Representative examples of plasticizers that may be used to plasticize the membranes include triacetin, tributyl citrate, triethyl citrate, acetyl tri-n-butyl citrate, diethyl phthalate, castor oil, dibutyl sebacate, acetylated monoglycerides and the like or mixtures thereof. The plasticizer may comprise typically about 10-30% or about 5-15% based on the weight of dry polymer, depending on the use of polymer dispersions or solutions.

In general, it is desirable to prime the surface of the active containing particle before applying the pulsatile-release membrane coating by applying a thin hydroxypropyl methylcellulose (HPMC) film. A particularly useful plasticized HPMC seal coat is Opadry® Clear available from Colorcon. While HPMC is typically used, other primer or seal coats such as hydroxypropyl cellulose (HPC) can also be used.

Rapidly-dispersing microgranules useful herein can be prepared in accordance with the following procedure. One or more sugar alcohols and/or saccharides with an average particle size of not more than 30 μm and a disintegrant are granulated with approximately 20-25% water in a high shear granulator, wet milled, dried in a fluid bed equipment to produce rapidly dispersible microgranules of desired particle size (average particle size of not more than about 300 μm in accordance with methods disclosed in U.S. Pat. Application No. 200100114340 published on Aug. 16, 2001). The sugar alcohol may be selected from the group consisting of mannitol, sorbitol, xylitol, maltitol and the like while the saccharide may be selected from the group consisting of lactose, sucrose, maltose or as a mixture of two or more, each of which is characterized by an average particle size of not more than about 30 μm. In one embodiment the sugar alcohol and/or saccharide is present in the tablet in an amount of about 30 to 70% by weight.

A disintegrant may be selected from the group consisting of crospovidone (crosslinked PVP), sodium starch glycolate, crosslinked sodium carboxymethyl cellulose, calcium silicate, low substituted hydroxypropyl cellulose and mixtures thereof. The disintegrant is typically present in the tablet in an amount of about 1 to 10% by weight. The disintegrant has a particle size less than about 30 microns in one embodiment.

The present invention relates to multi-dose forms, i.e., drug products in the form of multi-particulate dosage forms (pellets, beads, granules or mini-tablets) or in other forms suitable for oral administration.

The following non-limiting theoretical examples illustrate the coated beads and ODT dosage forms comprising these coated beads manufactured in accordance with the invention would exhibit desired in vitro and in vivo drug release profiles and significantly reduce adverse events, resulting in improved patient adherence to dosing regimen and patient compliance.

EXAMPLE 1

IR Beads (drug load: approximately 20% as atomoxetine): Atomoxetine hydrochloride (960 g) would be slowly added to an aqueous solution of polyvinylpyrrolidone (160 g Povidone K-30) and mixed well. 25-30 mesh sugar spheres (2.8 kg) would be coated with the drug-layering formulation (1120 g) in a Glatt fluid bed granulator. The drug containing pellets would be dried, and a seal coat of Opadry Clear (80 g) would be applied.

SR Beads (drug load: approximately 17% as atomoxetine): Duplicate batches of SR beads would be produced by providing IR beads with a membrane coating of ethylcellulose (Ethocel Premium Standard 10 from Dow Chemical Company) plasticized with triethyl citrate for a weight gain of 7.5% (batch size: 4 kg) to demonstrate robustness of the manufacturing process.

EXAMPLE 2

IR beads of atomoxetine with a drug load of 20% (as atomoxetine) would be produced following Example 1.

Enteric Beads (drug load: approximately 18% as atomoxetine): Duplicate batches of TPR beads would be produced by providing IR beads with a membrane coating of hypromellose phthalate (HP-55 from Shin Etsu Chemical Company) plasticized with triethyl citrate at 10% based on the coating weight for a weight gain of 10% (batch size: 4 kg).

EXAMPLE 3

IR beads of atomoxetine with a drug load of 20% (as atomoxetine) would be produced following Example 1.

TPR Beads (drug load: approximately 18% as atomoxetine): The lag-time coating would be applied on IR beads (3600 g) by spraying a 98/2 acetone/water solution containing Ethocel (182 g) and HPMCP (160 g) and diethyl phthalate (58 g) to produce 4 kg of TPR beads with 10% lag-time coating.

EXAMPLE 4

IR beads of atomoxetine with a drug load of 20% (as atomoxetine) would be produced following Example 1.

Taste-masked beads (drug load: approximately 16% as atomoxetine): IR beads (3200 g) would be coated in a fluid-bed equipment with a plasticized ethylcellulose for a membrane weight gain of 20%.

EXAMPLE 5

IR Beads (drug load: approximately 25% as atomoxetine): Atomoxetine hydrochloride (1200 g) would be slowly added to an aqueous solution of polyvinylpyrrolidone (200 g Povidone K-30) and mixed well. 60-80 mesh sugar spheres (2520 g) would be coated with the drug-layering formulation (1400 g) in a Glatt fluid bed granulator. The drug containing pellets would be dried, and a seal coat of Opadry Clear (80 g) would be applied.

TPR Beads (drug load: approximately 21.25% as atomoxetine): The lag-time coating would be applied on IR beads (3400 g) by spraying a 98/2 acetone/water solution containing Ethocel (273 g) and HPMCP (240 g) and diethyl phthalate (87 g) to produce 4 kg of TPR beads with 15% lag-time coating.

Rapidly-dispersible microgranules: The rapidly-dispersible microgranules comprising a sugar alcohol such as mannitol and a disintegrant such as crospovidone would be prepared following the procedure disclosed in the co-pending U.S. patent application Ser. No. 10/827,106 filed Apr. 19, 2004. Currently, D-mannitol (152 kg) with an average particle size of approximately 20 μm or less (Pearlitol 25 from Roquette, France) is blended with 8 kg of cross-linked povidone (Crospovidone XL-10 from ISP) in a high shear granulator (GMX 600 from Vector) and granulated with purified water (approximately 32 kg) and wet-milled using Comil from Quadro and dried in Glatt GPCG 200. The rapidly-dispersible microgranules thus obtained would have an average particle size in the range of approximately 125-200 μm.

Atomoxetine Hydrochloride Orally Disintegrating Tablets: Rapidly-dispersible microgranules (16.17 kg) would be blended with TPR beads (3.0 kg) and other pharmaceutical acceptable ingredients (0.83 kg), such as flavor, sweetener, colorant, and additional disintegrant in sufficient quantity to provide a therapeutically effective unit dose, in a twin shell V-blender for a sufficient time to get homogeneously distributed blending for compression. Tablets weighing approximately 400 mg would be compressed using a production scale tablet press equipped with an external lubrication system at a mean hardness of about 7 kP. Atomoxetine Hydrochloride ODT, 10, 20 and 40 mg (as atomoxetine) would also be produced by blending appropriate amounts of the coated beads (weight proportional to dose strength) with rapidly-dispersing microgranules at a ratio of coated beads to microgranules of from about 1:8 to about 1:2 and compressing the blends thus obtained.

EXAMPLE 6

Taste-masked and TPR Beads: IR beads containing atomoxetine HCl at 25% (as atomoxetine) drug-load would be prepared following Example 5. Taste-masked IR Beads (drug load: approximately 20% as atomoxetine) would be prepared following Example 4. Also, TPR beads containing atomoxetine HCl at 21.25% (as atomoxetine) drug-load would be prepared following Example 5. The rapidly-dispersible microgranules comprising a sugar alcohol such as mannitol and a disintegrant such as crospovidone would be prepared following Example 5.

Atomoxetine Hydrochloride Orally Disintegrating Tablets: Rapidly-dispersible microgranules (16.13 kg) would be blended with taste-masked beads (785 g) and TPR beads (2.22 kg) and other pharmaceutical acceptable ingredients (865 g), such as flavor, sweetener, colorant, and additional disintegrant in sufficient quantity to provide a therapeutically effective unit dose, in a twin shell V-blender for a sufficient time to get homogeneously distributed blending for compression. 60 mg tablets weighing approximately 400 mg would be compressed using a production scale rotary tablet press equipped with an external lubrication system at a mean hardness of about 7 kP.

Drug Release Testing: The drug release profiles would be generated by dissolution testing per US Pharmacopoeia dissolution procedure (USP Apparatus 1, Baskets@ 100 rpm using 700 mL of pH 1.2 buffer for 2 hours followed by additional testing in 900 mL of pH 6.8).

Based on the analytical data, minor changes to the drug-loading and/or coating levels may be easily implemented. Using the already established manufacturing process for rapidly-dispersing microgranules, orally disintegrating tablets (ODTs) will be produced and analytically tested to confirm the taste-masking and rapidly-releasing properties. Clinical studies will be conducted to confirm the beneficial effects that these new dosage forms bring to patients, especially to pediatric patients, thereby resulting in significant improvement in patient compliance and efficacy.

Changes may be made by persons skilled in the art in the compositions of various components of the finished dosage form (ODT) and/or in the steps or the sequence of steps of the method of manufacture described therein without departing from the spirit and scope of the invention as defined in the following claims.

What is claimed is:

1. A multiparticulate pharmaceutical composition comprising:
   (a) a plurality of timed, pulsatile-release (TPR) beads, wherein the TPR beads comprise drug-containing particles comprising atomoxetine or a pharmaceutically acceptable salt thereof,
   wherein said drug-containing particles are coated with a TPR membrane comprising a blend of a water-insoluble polymer and an enteric polymer.

2. The pharmaceutical composition of claim 1 further comprising:
   (b) rapidly-dispersing microgranules comprising a disintegrant and a sugar alcohol or a saccharide or a combination thereof, wherein the sugar alcohol or saccharide has an average particle diameter of not more than about 30 μm, and
   wherein the pharmaceutical composition is in the form of an orally disintegrating tablet.

3. The pharmaceutical composition of claim 1, further comprising taste-masked beads comprising IR beads coated with a taste-masking membrane,
   wherein said IR beads comprise atomoxetine or a pharmaceutically acceptable salt thereof and said taste-masking membrane comprises a water-insoluble polymer.

4. The pharmaceutical composition of claim 3, wherein said taste-masked beads and TPR beads are present in said pharmaceutical composition at a ratio of taste-masked beads to TPR beads of from about 30:70 to about 90:10 by weight.

5. The pharmaceutical composition of claim 2, wherein the ratio of rapidly-dispersing microgranules to TPR beads or the ratio of rapidly-dispersing microgranules to a combination of TPR beads and taste-masked beads is within the range of from about 9:1 to 2:1 by weight, and
   wherein said taste-masked beads comprise IR beads coated with a taste-masking membrane, and said IR beads comprise atomoxetine or a pharmaceutically acceptable salt thereof and said taste-masking membrane comprises a water-insoluble polymer.

6. The pharmaceutical composition of claim 5, wherein said orally disintegrating tablet disintegrates on contact with the saliva in the buccal cavity within about 60 seconds.

7. The pharmaceutical composition of claim 1, wherein said water insoluble polymer is selected from the group consisting of ethylcellulose, cellulose acetate, cellulose acetate butyrate, polyvinyl acetate, neutral methacrylate acid copolymers and mixtures thereof.

8. The pharmaceutical composition of claim 3, wherein said taste-masking membrane comprises a water-insoluble ethylcellulose or polyvinyl acetate and the membrane is present in an amount of about 5% to about 40% based on the total weight of the coated bead.

9. The pharmaceutical composition of claim 1, wherein said TPR membrane comprises a water-insoluble polymer and an enteric polymer at a weight ratio of from about 10:1 to about 1:1.

10. The pharmaceutical composition of claim 1, wherein said TPR membrane is present in an amount of about 10% to about 60% based on the total weight of the coated TPR bead.

11. The pharmaceutical composition of claim 1, wherein said TPR membrane further comprises a plasticizer selected from the group consisting of triacetin, tributyl citrate, tri-ethyl citrate, acetyl tri-n-butyl citrate, diethyl phthalate, dibutyl sebacate, polyethylene glycol, polypropylene glycol, castor oil and acetylated mono- and di-glycerides and mixtures thereof.

12. The pharmaceutical composition of claim 1, wherein said drug-containing particles comprise inert particles coated with atomoxetine or a pharmaceutically acceptable salt thereof in a polymeric binder selected from the group consisting of hydroxypropyl cellulose, hydroxypropyl methylcellulose, polyvinylpyrrolidone and mixtures thereof.

13. The pharmaceutical composition of claim 12, wherein said inert particle is selected from the group consisting of sugar spheres, cellulose spheres, and silicone dioxide spheroids.

14. The pharmaceutical composition of claim 2, wherein said disintegrant is selected from the group consisting of crosslinked polyvinyl pyrrolidone, crosslinked sodium carboxymethylcellulose, sodium starch glycolate, low-substituted hydroxypropylcellulose and mixtures thereof.

15. The pharmaceutical composition of claim 2, wherein said sugar alcohol or saccharide is selected from the group consisting of mannitol, xylitol, sorbitol, maltol, lactose, sucrose and mixtures thereof.

16. The pharmaceutical composition of claim 3, wherein said taste-masked beads release substantially all of the atomoxetine contained in said taste-masked beads within about 2 hours following oral administration.

17. The dosage form of claim 16 wherein said TPR beads release substantially all of the atomoxetine contained in said TPR beads within about 4 hours following a lag-time of approximately 1 to 6 hours following oral administration.

18. The pharmaceutical composition of claim 1, in the form of a dosage form containing a total of from about 10 mg to 60 mg of atomoxetine.

19. A method for the preparation of multi-particulate pharmaceutical dosage form comprising the steps of:
   (a) preparing rapidly-dispersing microgranules by granulating a powder mixture comprising a sugar alcohol or a saccharide or a combination thereof having an average particle diameter of not more than about 30 μm and a disintegrant, (b) preparing TPR beads by applying to drug-containing particles comprising atomoxetine or a pharmaceutically acceptable salt thereof, a TPR coating comprising a combination of a water-insoluble polymer and an enteric polymer, thereby providing an in-vitro lag-time of about 1 to 6 hours, (c) optionally, preparing taste-masked beads by coating drug-containing particles with a water-insoluble polymer, thereby providing taste-masking properties, (d) blending rapidly dispersing microgranules from step (a), TPR beads from step (b) and optionally taste-masked beads from step (c), and (e) compressing the blend from step (d) to form an orally disintegrating tablet.

20. The method of claim 19 wherein the drug-containing particles are prepared by layering atomoxetine or a pharmaceutically acceptable salt thereof from a polymeric binder solution on inert particles selected from the group consisting of sugar spheres, cellulose spheres, and silicon dioxide spheroids.

21. The method of claim 19 wherein said TPR coating comprises ethylcellulose in combination with hypromellose phthalate.

22. The method of claim 21 wherein ethylcellulose and hypromellose phthalate are present at a weight ratio of from about 10:1 to about 1:1.

23. The method of claim 22 wherein said TPR coating is present in an amount of from about 10% to about 60% based on the total weight of the coated TPR bead.

24. A method for treating a patient which comprises administering to the patient the pharmaceutical composition of claim 1.

25. The method of claim 24 wherein said patient is a child or adolescent being treated for ADHD.

26. The pharmaceutical composition of claim 1, wherein said enteric polymer is selected from the group consisting of cellulose acetate phthalate, cellulose acetate succinate, polyvinyl acetate phthalate, hypromellose phthalate, anionic methacrylic acid copolymers and mixtures thereof.

27. The pharmaceutical composition of claim 1, wherein said TPR membrane provide release of the drug after a lag time of about 1-6 hours following oral administration.

28. The method of claim 19, wherein the TPR beads provide a lag time of about 1 to 6 hours.

29. The method of claim 19, wherein the method comprises
(c) preparing taste-masked beads by coating drug-containing particles with a water-insoluble polymer, and
wherein the ratio of TPR beads from step (b) to taste-masked beads of step (c) is about 70/30 to 100/0.

* * * * *

UNITED STATES PATENT AND TRADEMARK OFFICE
CERTIFICATE OF CORRECTION

| | | |
|---|---|---|
| PATENT NO. | : 8,747,895 B2 | Page 1 of 1 |
| APPLICATION NO. | : 11/223819 | |
| DATED | : June 10, 2014 | |
| INVENTOR(S) | : Venkatesh et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1671 days.

Signed and Sealed this
Twentieth Day of October, 2015

Michelle K. Lee
*Director of the United States Patent and Trademark Office*